United States Patent
Korenev et al.

(10) Patent No.: US 6,933,733 B2
(45) Date of Patent: *Aug. 23, 2005

(54) METHOD AND APPARATUS FOR MEASURING THE CONCENTRATION OF HYDROGEN PEROXIDE IN A FLUID

(75) Inventors: Sergey A. Korenev, Mundelein, IL (US); Ivan S. Korenev, Mundelein, IL (US); Michael A. Centanni, Parma, OH (US)

(73) Assignee: STERIS Inc., Temecula, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/667,988

(22) Filed: Sep. 22, 2003

(65) Prior Publication Data

US 2004/0178799 A1 Sep. 16, 2004

Related U.S. Application Data (63) Continuation-in-part of application No. 10/389,036, filed on Mar. 14, 2003, now Pat. No. 6,844,742.

(51) Int. Cl.[7] .......................... G01R 27/26; G01R 27/08
(52) U.S. Cl. ........................................ 324/663; 324/691
(58) Field of Search ................................. 324/663, 664, 324/691–698, 658–662, 453, 439–450; 204/403.01, 416, 431; 205/775, 777, 778.5, 782, 789

(56) References Cited

U.S. PATENT DOCUMENTS 3,636,444 A    1/1972  Strawn et al. ............ 324/61 R
3,778,706 A   12/1973  Thompson ................ 324/61 R
3,816,811 A *  6/1974  Cmelik ....................... 324/667

(Continued)

OTHER PUBLICATIONS

U.S. Appl. No. 10/389,036, filed Mar. 14, 2003, Centanni, entitled: Method and Apparatus for Measuring Chemical Concentration in a Fluid.

U.S. Appl. No. 10/405,880, filed Apr. 2, 2003, Centanni, entitled: Method and Apparatus for Measuring Concentration of a Chemical Component in a Gas Mixture.

(Continued)

*Primary Examiner*—Anjan Deb
*Assistant Examiner*—Amy He
(74) *Attorney, Agent, or Firm*—Kusner & Jaffe; Michael A. Centanni (57) ABSTRACT

A method and apparatus for measuring the concentration of hydrogen peroxide in a liquid or gaseous fluid. A capacitor is exposed to the fluid, wherein the fluid acts as the dielectric between the conductors of the capacitor. The permittivity and dielectric constant associated with the fluid is affected by the relative concentrations of the chemical components comprising the fluid. A measurement of the capacitance is used to determine the relative concentration levels of the chemical components in the fluid. In an alternative embodiment, a resistor, and associated resistance values, are used to determine the concentration of hydrogen peroxide in a liquid or gaseous fluid.

20 Claims, 7 Drawing Sheets

U.S. PATENT DOCUMENTS

| | | |
|---|---|---|
| 4,031,742 A | 6/1977 | Michael et al. ............... 73/40.7 |
| 4,158,810 A * | 6/1979 | Leskovar ..................... 324/127 |
| 4,219,776 A | 8/1980 | Arulanandan ................ 324/323 |
| 4,427,772 A | 1/1984 | Kodera et al. ................. 435/27 |
| 4,509,522 A | 4/1985 | Manuccia et al. ........... 128/634 |
| 4,525,265 A | 6/1985 | Abe et al. .................... 204/403 |
| 4,674,879 A | 6/1987 | Gregorig et al. ............. 356/301 |
| 4,769,593 A | 9/1988 | Reed et al. .................. 324/668 |
| 4,849,687 A | 7/1989 | Sims et al. ................... 324/668 |
| 4,857,152 A | 8/1989 | Armstrong et al. .......... 204/1 T |
| 5,151,660 A | 9/1992 | Powers et al. ............... 324/689 |
| 5,157,968 A | 10/1992 | Zfira ............................ 73/149 |
| 5,171,523 A | 12/1992 | Williams ...................... 422/20 |
| 5,179,926 A | 1/1993 | Ament ......................... 123/494 |
| 5,243,858 A | 9/1993 | Erskine et al. ............ 73/204.26 |
| 5,364,510 A | 11/1994 | Carpio ..................... 204/153.1 |
| 5,439,569 A | 8/1995 | Carpio ..................... 204/153.1 |
| 5,459,568 A | 10/1995 | Yano et al. .................. 356/336 |
| 5,470,754 A | 11/1995 | Rounbehler et al. ......... 436/106 |
| 5,600,142 A | 2/1997 | Van Den Berg et al. ...................... 250/339.13 |
| 5,847,276 A | 12/1998 | Mimken et al. ............... 73/453 |
| 5,882,590 A | 3/1999 | Stewart et al. ................. 422/28 |
| 5,997,685 A | 12/1999 | Radhamohan et al. ....... 156/345 |
| 6,162,409 A | 12/2000 | Skelley et al. ............ 423/239.1 |
| 6,369,387 B1 | 4/2002 | Eckles .......................... 250/343 |
| 6,454,874 B1 | 9/2002 | Jacobs et al. .................. 134/18 |
| 6,614,242 B2 | 9/2003 | Matter et al. ................ 324/698 |
| 6,660,231 B2 | 12/2003 | Moseley ........................ 422/98 |
| 6,706,648 B2 | 3/2004 | Yamazaki et al. ............ 438/790 |
| 2002/0014410 A1 * | 2/2002 | Silveri et al. ................ 204/412 |
| 2002/0033186 A1 | 3/2002 | Verhaverbeke et al. ........ 134/26 |
| 2002/0076492 A1 | 6/2002 | Loan et al. ............. 427/255.28 |
| 2002/0109511 A1 | 8/2002 | Frank .......................... 324/663 |
| 2002/0111040 A1 | 8/2002 | Yamazaki et al. ........... 438/783 |
| 2002/0157686 A1 | 10/2002 | Kenny et al. ................. 134/1.3 |
| 2003/0063997 A1 | 4/2003 | Fryer et al. ..................... 422/3 |
| 2003/0102007 A1 | 6/2003 | Kaiser ........................... 134/1 |
| 2003/0157587 A1 | 8/2003 | Gomez et al. ................. 435/30 |
| 2004/0029257 A1 | 2/2004 | Dutil et al. .................. 435/266 |
| 2004/0079395 A1 | 4/2004 | Kim et al. ..................... 134/30 |
| 2004/0178802 A1 | 9/2004 | Centanni .................... 324/662 |
| 2004/0178804 A1 | 9/2004 | Allen et al. ................. 324/662 |
| 2004/0262170 A1 | 12/2004 | Centanni .................... 205/782 |

U.S. Appl. No. 10/456,378, filed Jun. 6, 2003, Centanni, entitled: Method and Apparatus for Formulating and Controlling Chemical Concentrations in a Solution.

U.S. Appl. No. 10/456,380, filed Jun. 6, 2003, Centanni, entitled: Method and Apparatus for Formulating and Controlling Chemical Concentrations in a Gas Mixture.

Philipp, "*Charge Transfer Sensing,*" 1997.

Wojslaw, "*Everything You Wanted to Know About Digitally Programmable Potentiometers,*" Catalyst Semiconductor, Inc., Oct. 17, 2001, Publication No. 6009.

Kittel, "*Introduction to Solid State Physics,*" Fourth Edition, John Wiley & Sons, Inc., 1971.

Philipp, "*The Charge Transfer Sensor,*" Sensors Magazine, Oct. 1999.

T. J. Buckley et al., "*Toroidal Cross Capacitor for Measuring the Dielectric Constant of Gases,*" Review of Scientific Instruments, vol. 71, No. 7, Jul. 2000, pp. 2914–2921.

Gross et al., "*The Dielectric Constants of Water Hydrogen Peroxide and Hydrogen Peroxide–Water Mixtures,*" L. Amer. Chem. Soc., vol. 72, 1950, pp. 2075–2080.

"*Humidity Sensor Theory and Behavior,*" Psychometrics and Moisture, Honeywell HVAC, Nov. 27, 2002.

U.S. Appl. No. 10/872,227, filed Jun. 18, 2004, Kaiser et al., entitled: Method and Apparatus for Monitoring the Purity and/or Quality of Steam.

U.S. Appl. No. 10/896,609, filed Jul. 21, 2004, Kaiser et al., entitled: Method and Apparatus for Real Time Monitoring of Metallic Cation Concentrations in a Solution.

U.S. Appl. No. 10/900,745, filed Jul. 28, 2004, Kaiser et al., entitled: Method and Apparatus for Monitoring the State of a Chemical Solution for Decontamination of Chemical and Biological Warfare Agents.

U.S. Appl. No. 10/931,186, filed Aug. 31, 2004, Kaiser et al., entitled: Method and Apparatus for Monitoring Detergent Concentration in a Decontamination Process.

* cited by examiner

METHOD AND APPARATUS FOR MEASURING THE CONCENTRATION OF HYDROGEN PEROXIDE IN A FLUID

RELATED APPLICATIONS

The present invention is a Continuation-In-Part (CIP) of U.S. application Ser. No. 10/389,036, filed Mar. 14, 2003, now U.S. Pat. No. 6,844,742, entitled "Method and Apparatus for Measuring Chemical Concentration in a Fluid," which is incorporated herein by reference in its entirety.

FIELD OF THE INVENTION

The present invention relates generally to determining a chemical concentration, and more particularly to a method and apparatus for measuring the concentration of hydrogen peroxide in a liquid or gaseous fluid.

BACKGROUND OF THE INVENTION

There are many applications in which is desirable or necessary to obtain a measurement of the concentration of a chemical component (e.g., hydrogen peroxide) in a fluid, including, but not limited to, a liquid and vapor sterilization system. Several techniques have been developed in the prior art to measure the concentration of hydrogen peroxide ($H_2O_2$) in a fluid. These techniques include the use of electrochemical sensors (e.g., an amperometric electrode coated with a hydrophilic or hydrophobic membrane), infrared sensors, color indicators, radio-frequency systems, gas analyzers, and spectroscopy (e.g., photometric infrared).

The dielectric constant (K) of a dielectric material is related to the permittivity ($\epsilon$) of the dielectric material by the relationship $K=\epsilon/\epsilon_0$, where $\epsilon_0$ is the permittivity of free space. In accordance with this relationship, changes to the permittivity ($\epsilon$) of the dielectric material result in changes to the dielectric constant (K) of the dielectric material.

The present invention provides a method and apparatus for determining chemical concentrations using changes in the permittivity and dielectric constant of a dielectric material.

SUMMARY OF THE INVENTION

In accordance with a first aspect of the present invention, there is provided a chemical concentration measuring system for determining a concentration of hydrogen peroxide in a fluid comprised of at least one chemical component, comprising: (1) a capacitive voltage divider circuit including: (a) a first capacitor having first and second conductors exposed to the fluid, said fluid comprising a dielectric therebetween, and (b) a second capacitor; (2) an alternating current (AC) voltage generator for applying an AC voltage to the capacitive voltage divider circuit; and (3) processing means for measuring a voltage across the second capacitor to determine a first capacitance of the first capacitor, and determining the concentration of the hydrogen peroxide in the fluid in accordance with the first capacitance.

In accordance with another aspect of the present invention, there is provided a chemical concentration measuring system for determining a concentration of hydrogen peroxide in a fluid comprised of at least one chemical component, comprising: (1) a resistive voltage divider circuit including: (a) a first resistor including first and second conductors exposed to the fluid, said fluid comprising a resistive element of the first resistor, and (b) a second resistor; (2) an alternating current (AC) voltage generator for applying an AC voltage to the resistive voltage divider circuit; and (3) processing means for measuring a voltage across the second resistor to determine a first resistance of the first resistor, and determining the concentration of the hydrogen peroxide in the fluid in accordance with the first resistor.

In accordance with still another aspect of the present invention, there is provided a method for determining a concentration of hydrogen peroxide in a fluid having at least on chemical component, comprising: (a) exposing a capacitor having first and second conductors to the fluid, said fluid comprising a dielectric therebetween; and (b) determining a change in an electrical property of the capacitor associated with the capacitor, said change in the electrical property varying according to the concentration of the hydrogen peroxide in the fluid.

In accordance with yet another aspect of the present invention, there is provided a method for determining a concentration of hydrogen peroxide in a fluid having at least on chemical component, comprising: (a) exposing a resistor having first and second terminal to the fluid, said fluid comprising a resistive element of the resistor; and (b) determining a change in an electrical property of the resistor, said change in the electrical property varying according to the concentration of the hydrogen peroxide in the fluid.

An advantage of the present invention is the provision of a method and apparatus for measuring the concentration of hydrogen peroxide in a fluid, wherein the fluid may be a liquid or a gas (e.g., vapor).

Another advantage of the present invention is the provision of a method and apparatus for measuring the concentration of hydrogen peroxide in a fluid that uses the fluid as the dielectric of a capacitor.

Still another advantage of the present invention is the provision of a method and apparatus for measuring the concentration of hydrogen peroxide in a fluid that uses the resistive properties of the fluid to form a resistor in the fluid.

Still another advantage of the present invention is the provision of a chemical concentration measuring system that is simple and inexpensive to manufacture.

Yet another advantage of the present invention is the provision of a chemical concentration measuring system that can be suitably used to determine the concentration of liquid hydrogen peroxide in the feed stream to a vaporizer, in a biocontamination deactivation apparatus.

These and other advantages will become apparent from the following description of a preferred embodiment taken together with the accompanying drawings and the appended claims.

BRIEF DESCRIPTION OF THE DRAWINGS

The invention may take physical form in certain parts and arrangement of parts, a preferred embodiment of which will be described in detail in the specification and illustrated in the accompanying drawings which form a part hereof, and wherein.

DETAILED DESCRIPTION OF A PREFERRED EMBODIMENT

Figure 1:
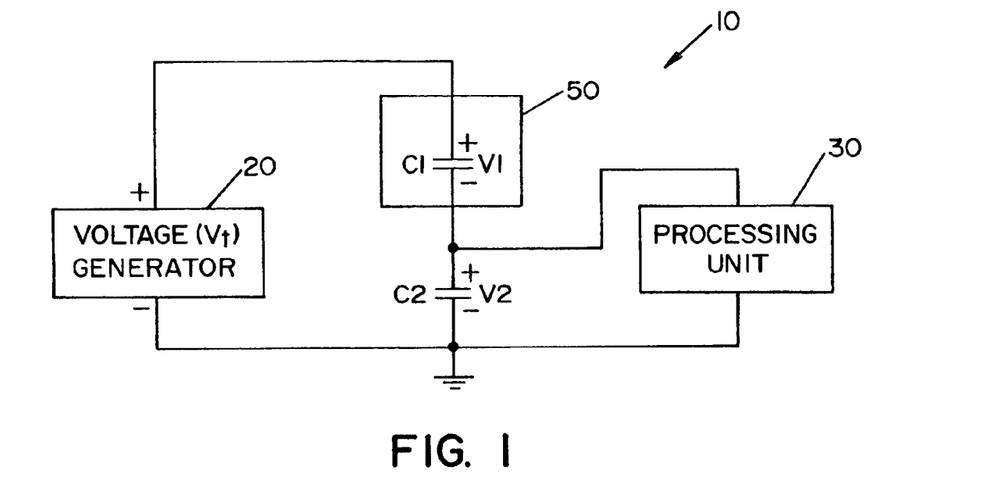
FIG. 1 is a schematic diagram illustrating a chemical concentration measuring system having a capacitive voltage divider circuit, according to a preferred embodiment of the present invention.

Referring now to the drawings wherein the showings are for the purposes of illustrating a preferred embodiment of the invention only and not for purposes of limiting same, FIG. 1 shows a schematic of a chemical concentration measuring system 10 according to a preferred embodiment of the present invention. In accordance with a preferred embodiment of the present invention, chemical concentration measuring system 10 determines the concentration of hydrogen peroxide in a fluid, wherein the fluid may be in the form of a liquid fluid or a gaseous fluid.

It should be understood that the term "gaseous" fluid includes vaporous fluids (i.e., liquids in a vapor state). In accordance with a preferred embodiment, the liquid fluid is comprised of liquid hydrogen peroxide in combination with a diluent or liquid oxidant. In the embodiment illustrated herein, the liquid fluid is comprised of liquid hydrogen peroxide and water. In accordance with a preferred embodiment, the gaseous fluid is comprised of vaporized hydrogen peroxide in combination with at least one of air, water vapor, ozone, or other gaseous oxidant. Alternatively, the gaseous fluid may simply be comprised of vaporized hydrogen peroxide in a vacuum.

Figure 6A:
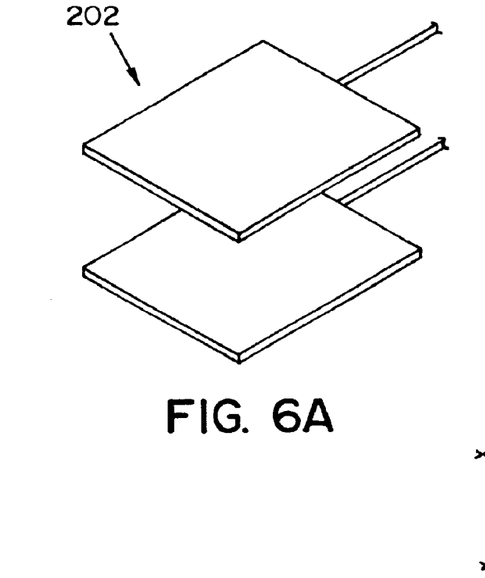
FIG. 6A illustrates a conventional parallel plate capacitor formed of a pair of solid parallel plates.
Figure 6B:
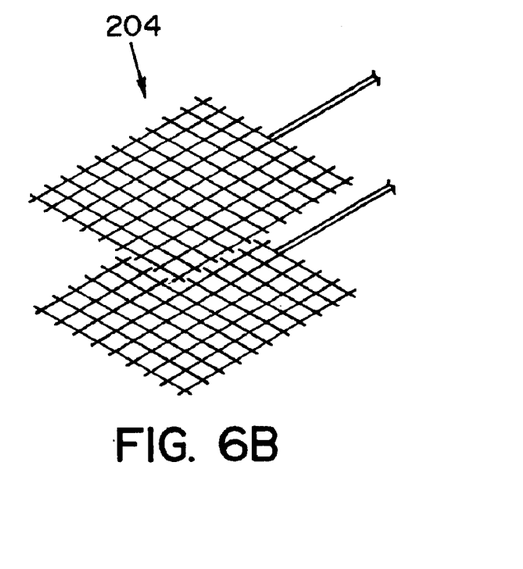
FIG. 6B illustrates a parallel plate capacitor formed of a pair of metal net plates.
Figure 7:
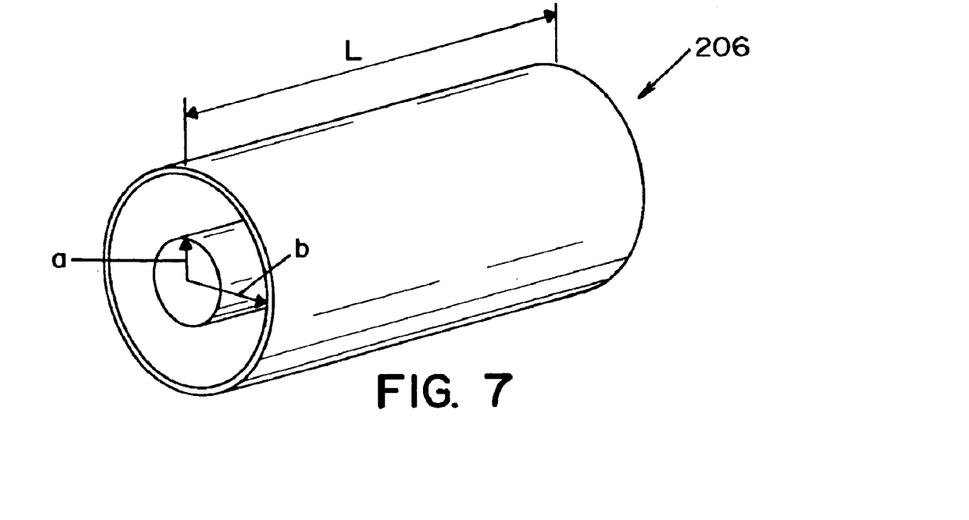
FIG. 7 illustrates a conventional cylindrical capacitor.

Chemical concentration measuring system 10 is generally comprised of an input voltage generator 20, a capacitor C1, a capacitor C2, and a processing unit 30. In accordance with a preferred embodiment capacitors C1 and C2 are arranged to form a "capacitive" voltage divider circuit, as will be described in further detail below. Capacitors C1 and C2 can be constructed in various forms, including but not limited to, parallel plate capacitors, cylindrical capacitors, and spherical capacitors. If a spherical capacitor is used as a sensing capacitor, holes must be placed in the outer shell of the capacitor such that a fluid can enter and exit the capacitor. FIG. 6A illustrates a conventional parallel plate capacitor 202 formed of a pair of solid parallel plates, while FIG. 6B illustrates a parallel plate capacitor 204 formed of a pair of metal net plates. FIG. 7 illustrates a conventional cylindrical plate capacitor 206 having dimensions a, b and L.

Input voltage generator 20 produces an alternating current (AC) input voltage signal, preferably in the form of bi-polar pulses, or radio-frequency (RF) sinusoidal oscillations. The input voltage is applied to capacitors C1 and C2. In a preferred embodiment, capacitor C1 acts as a sensing element, and is directly exposed to a liquid or gaseous fluid, such as a decontamination solution comprised of two or more chemical components. Capacitor C1 is located in a conduit, vessel, tank or chamber 50, wherein a fluid fills the gap between the conductors of capacitor C1, thereby acting as the insulator or "dielectric" of capacitor C1.

Processing unit 30 measures voltage V2 across capacitor C2. In the illustrated embodiment, capacitor C2 is outside the fluid, and has air as a dielectric material. In a preferred embodiment, processing unit 30 may take the form of a microcomputer or microcontroller, including a memory for data storage. Processing unit 30 may also be used to control the operation of other system elements, such as flow controls for controlling the flow of chemical components into conduit, vessel, tank or chamber 50.

Chemical concentration measuring system 10 uses the permittivity and dielectric constant associated with the fluid to determine the relative concentration of a chemical component in the fluid. Fluid fills the gap between the conductors of capacitor C1, thereby acting as the dielectric of capacitor C1. By arranging capacitors C1 and C2 to form a "capacitive" voltage divider circuit, a measure of voltage V2 across capacitor C2 can be used to determine capacitance C1. Capacitance C1 is indicative of the relative concentrations of the chemical components in the fluid, since the permittivity and dielectric constant of the fluid is affected by the relative concentrations of the chemical components in the fluid. It should be appreciated that a preferred embodiment of the present invention is described below wherein capacitor C1 is a parallel plate capacitor.

As will be readily appreciated by those skilled in the art:

$V_t = V1 + V2$ (Kirchoff's law)

$C1 = Q/V1$, $C2 = Q/V2$, and $C_t = Q/V_t$ where C1 is the capacitance of capacitor C1, C2 is the capacitance of capacitor C2, and $C_t$ is the total equivalent capacitance of series capacitors C1 and C2.

Since $V = Q/C$ and $V_t = V1 + V2$, $Q/C_t = Q/C1 + Q/C2$ $1/C_t = 1/C1 + 1/C2$ $C_t = (C1 C2)/(C1 + C2)$ Since $V1=Q/C1$, and $Q=C_tV_t$, $$V1 = (C_tV_t)/C1 = [[C1C2]/[(C1)(C1+C2)]][V_t]$$
$$= V_t[C2/(C1+C2)]$$
$$= V_t/[(C1/C2)+1]$$

Likewise, since $V2=Q/C2$, and $Q=C_tV_t$, $$V2 = (C_tV_t)/C2 = [[C1C2]/[(C2)(C1+C2)]][V_t]$$
$$= V_t[C1/(C1+C2)]$$
$$= V_t/[1+(C2/C1)]$$

Therefore, C1 can be determined from C2, V2 and $V_t$ according to the relationship:

$$C1=[(V2)(C2)]/[V_t-V2]$$

Furthermore, $k=C2/(C1+C2)$ for capacitor C1, thus $V1=(V_t)(k)$, where k is referred to herein as the "capacitor divider factor." For a capacitor having parallel plate conductors, $$C=(\epsilon)(A/d),$$

where, $\epsilon$ is the permittivity (Farads/meter) of the capacitor dielectric, A is the area of the parallel plates (m$^2$), and d is the separation in meters between the capacitor plates.

As $\epsilon$ increases, the capacitance C will increase. In view of the foregoing, factor k can be expressed as follows for capacitor C1:

$$k=[\epsilon_2(A2/d2)]/[(\epsilon_1(A1/d1))+(\epsilon_2(A2/d2))]$$

Since the area (A1) of capacitor plates of capacitor C1 equals the area (A2) of capacitor plates of capacitor C2, and the separation (d1) of the capacitor C1 plates equals separation (d2) of the capacitor C2 plates, $$k=(\epsilon_2)/(\epsilon_1+\epsilon_2)$$

Since capacitor C2 is in air, $\epsilon_2 \sim \epsilon_0 \sim 8.85 \times 10^{-12}$ F/m (permittivity in free space)

$$k=\epsilon_0(\epsilon_1+\epsilon_0)$$

In view of the foregoing, factor k will decrease as the permittivity of the decontamination solution increases.

With reference to FIG. 7, it will be understood that where a cylindrical capacitor is used for capacitor C1, the capacitance of capacitor C1 can be expressed as:

$$C1=[2\pi K\epsilon_0 L]/[1n(a/b)],$$

where L is the length of the capacitor, K is the dielectric constant, and $\epsilon_0$ is the permittivity of free space.

Figure 2:
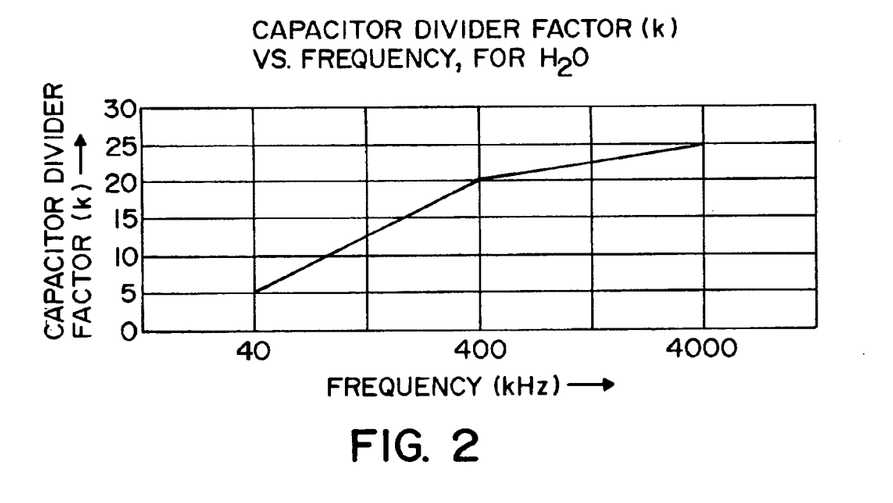
FIG. 2 is a graph illustrating the relationship between a factor of capacitor divider (k) and frequency, for de-ionized water.

With reference to FIG. 2, it will be observed that the response of a capacitor will be influenced by the characteristics (e.g., frequency) of the AC waveform applied thereto. In this regard, capacitive reactance ($X_c$) is a function of frequency. Capacitive reactance is the opposition offered to the flow of alternating current by pure capacitance, and is expressed in ohms ($X_c=1/(2\pi fC)$). In FIG. 2, capacitor C1 is a parallel plate capacitor that is exposed to a solution of 100% de-ionized water. The capacitor divider factor k ($k=C2/(C1+C2)$) is determined for a range of frequencies (40 kHz to 4000 kHz).

FIGS. 3, 4 and 5A–5D will now be described in detail. In connection with the data shown in these figures, it should be understood that references herein to "an aqueous solution of hydrogen peroxide" refers to a solution comprised of 35% hydrogen peroxide and 65% water (by weight).

Figure 3:
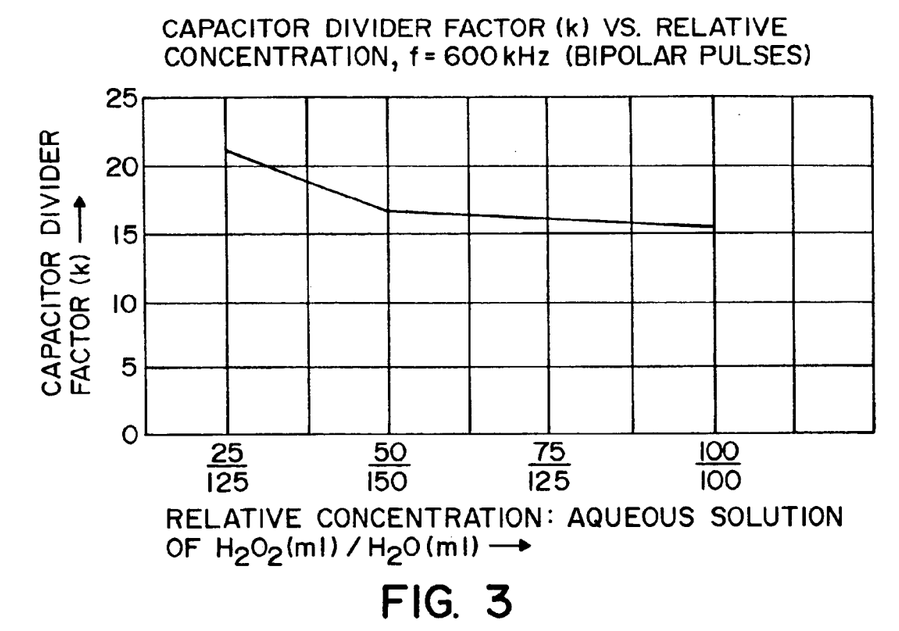
FIG. 3 is a graph illustrating the relationship between: (1) a factor of capacitor divider (k) and (2) relative concentrations of an aqueous solution of $H_2O_2$ (ml) and $H_2O$ (ml), at a frequency of 600 kHz (bipolar pulses)

Turning now to FIG. 3, capacitor C1 is a parallel plate capacitor exposed to a solution comprised of (a) an aqueous solution of hydrogen peroxide and (b) de-ionized water. Voltage generator 20 produces bipolar pulses at a frequency of 600 kHz. Capacitor divider factor k is determined for four (4) different relative concentrations of hydrogen peroxide and de-ionized water. As can be observed from FIG. 3, the capacitor divider factor k decreases, as the concentration of hydrogen peroxide increases. In this regard, $\epsilon_1$ increases as the concentration of hydrogen peroxide increases.

Figure 4:
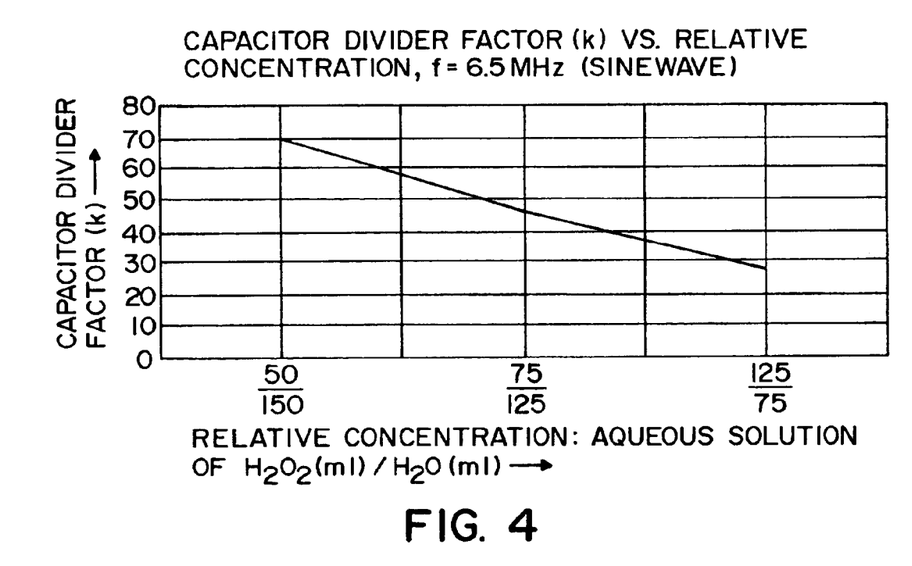
FIG. 4 is a graph illustrating the relationship between: (1) a factor of capacitor divider (k) and (2) relative concentrations of an aqueous solution of $H_2O_2$ (ml) and $H_2O$ (ml), at a frequency of 6.5 MHz (sinusoidal waveform)

Referring now to FIG. 4, capacitor C1 is a parallel plate capacitor exposed to a solution comprised of (a) an aqueous solution of hydrogen peroxide and (b) de-ionized water. Voltage generator 20 produces a sinusoidal waveform having a frequency of 6.5 MHz. Capacitor divider factor k is determined for three (3) different relative concentrations of an aqueous solution of hydrogen peroxide and de-ionized water. As noted above with respect to FIG. 3, the capacitor divider factor k decreases, as the concentration of the aqueous solution of hydrogen peroxide increases.

Figure 5A:
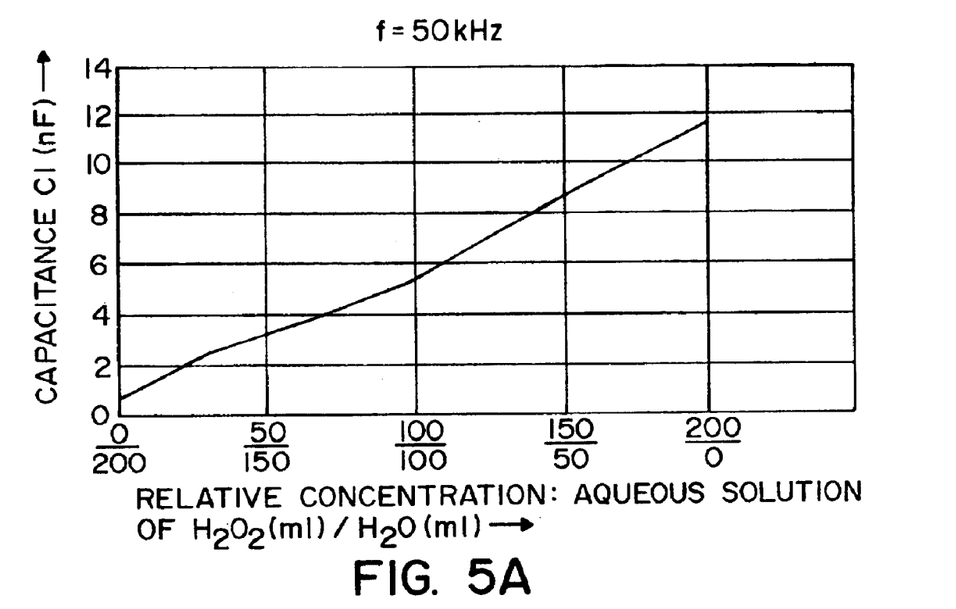
FIG. 5A is a graph illustrating the relationship between: (1) capacitance of capacitor C1 (nF) and (2) relative concentrations of an aqueous solution of $H_2O_2$ (ml) and $H_2O$ (ml), at a frequency of 50 kHz.
Figure 5B:
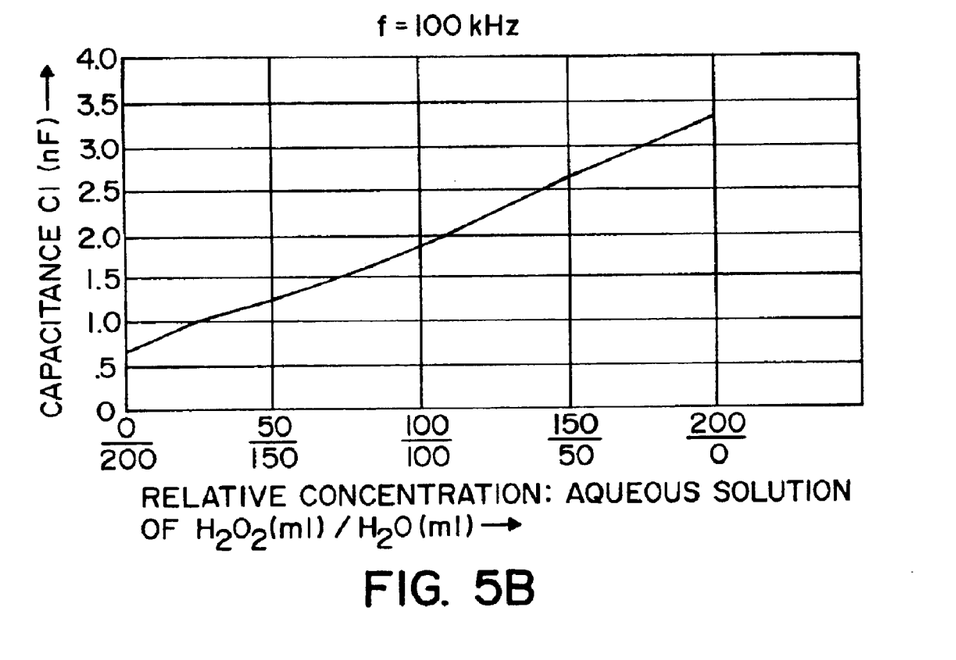
FIG. 5B is a graph illustrating the relationship between: (1) capacitance of capacitor C1 (nF) and (2) relative concentrations of an aqueous solution of $H_2O_2$ (ml) and $H_2O$ (ml), at a frequency of 100 kHz.
Figure 5C:
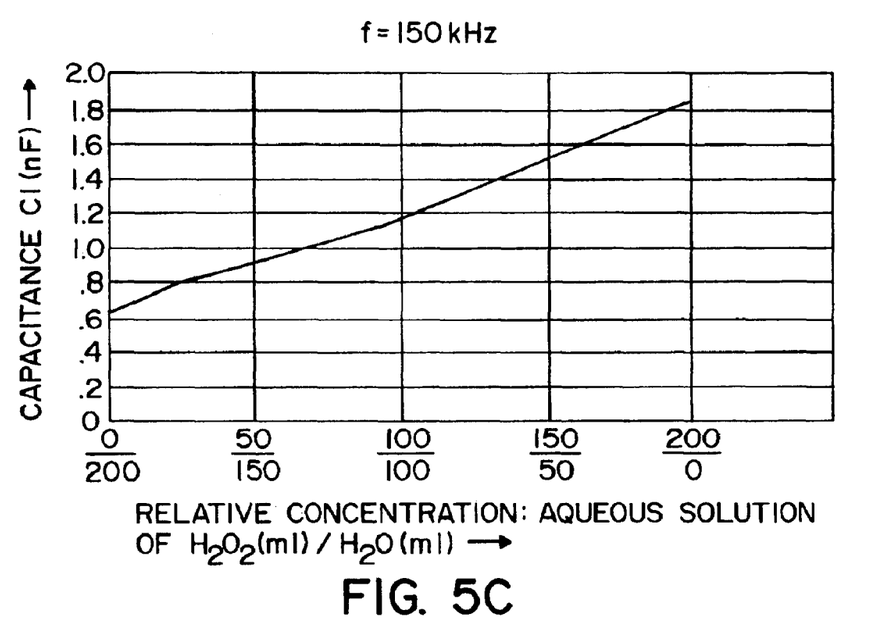
FIG. 5C is a graph illustrating the relationship between: (1) capacitance of capacitor C1 (nF) and (2) relative concentrations of an aqueous solution of $H_2O_2$ (ml) and $H_2O$ (ml), at a frequency of 150 kHz.
Figure 5D:
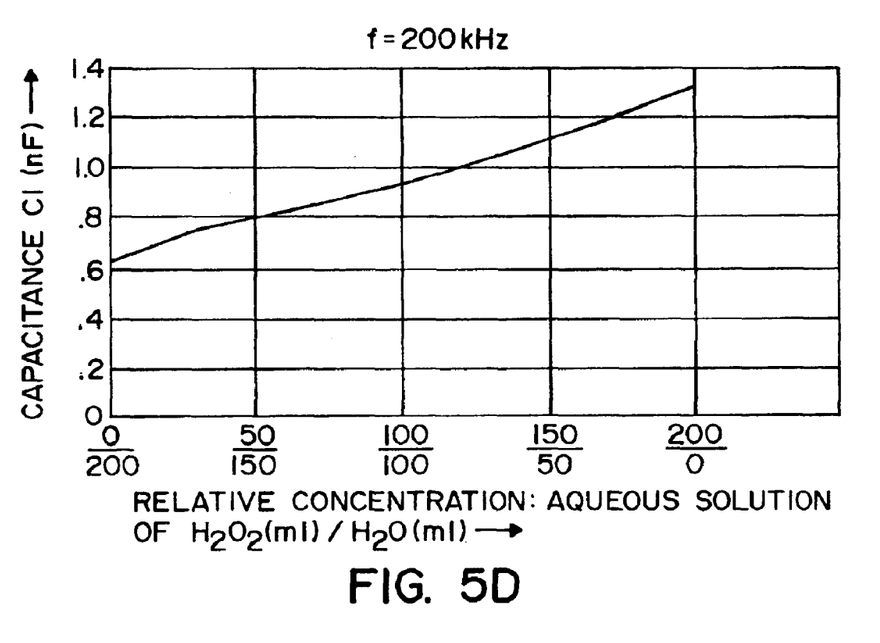
FIG. 5D is a graph illustrating the relationship between: (1) capacitance of capacitor C1 (nF) and (2) relative concentrations of an aqueous solution of $H_2O_2$ (ml) and $H_2O$ (ml), at a frequency of 200 kHz.

In FIGS. 5A–5D, capacitor C1 is a parallel plate capacitor exposed to a solution comprised of (a) an aqueous solution of hydrogen peroxide and (b) de-ionized water. Each plate of capacitor C1 has a radius of about 1 inch, and a separation d of about 0.5 inch. Voltage generator 20 produces a rectangular pulse form having a range of frequencies (i.e., 50 kHz, 100 kHz, 150 kHz and 200 kHz). Capacitance of capacitor C1 is determined for a range of relative concentrations of an aqueous solution of hydrogen peroxide and de-ionized water. As can be seen in FIGS. 5A–5D, capacitance of capacitor C1 increases as the concentration of the aqueous solution of hydrogen peroxide in the decontamination solution increases. A relatively linear relationship between the capacitance of capacitor C1 and the relative concentration of the aqueous solution of hydrogen peroxide and de-ionized water is observed with a frequency of 100 kHz (FIG. 5B).

Operation of chemical concentration measuring system 10, according to a preferred embodiment, will now be described in detail. As a preliminary step, processing unit 30 stores in memory a table of data comprising values of the capacitance of capacitor C1 for a plurality of relative concentrations of chemical components in a fluid. This table of data may be determined by exposing capacitor C1 to fluids having different relative concentrations of chemical components, and recording the corresponding measured capacitance C1. For example, processing unit 30 may store values of the capacitance of capacitor C1 that are determined for a plurality of fluids having different relative concentrations of an aqueous solution of hydrogen peroxide ($H_2O_2$) and de-ionized water ($H_2O$), as shown in FIG. 5B.

After the table of data is stored by processing unit 30, measurement of chemical concentrations for a fluid in conduit, vessel, tank or chamber 50 can commence. Capacitor C1 of chemical concentration measuring system 10 is exposed to a fluid that is being monitored. For instance, capacitor C1 may be located in a conduit, vessel, tank or chamber 50 filled with a liquid or gaseous fluid. A measurement of voltage V2 is used to determine a value for the capacitance of capacitor C1. The stored table is searched for the capacitance of capacitor C1 to obtain the corresponding relative chemical concentration. If the capacitance of capacitor C1 is not found in the table as a pre-stored value, the stored data is used to interpolate or extrapolate corresponding relative chemical concentrations of chemical components in the fluid. As will be noted with reference to FIG. 5B, at f=100 kHz, the relationship between the capacitance of capacitor C1 and relative concentrations of an aqueous solution of hydrogen peroxide and de-ionized water is generally linear. This linear relationship allows one to normalize any measurement made so as to provide the absolute concentration of the oxidant or sterilant in the de-ionized water.

Based upon the determined relative concentrations of the chemical components in the fluid, processing unit 30 may be programmed to control the concentration of one, or both, of the chemical components in the fluid. For instance, processing unit 30 may adjust a flow control valve to modify the relative concentrations in accordance with the determined relative concentrations. Accordingly, processing unit 30 may adjust the relative concentrations to correspond with desired relative concentrations that provide optimum decontamination. Processing unit 30 may also provide an audible and/or visual indicator to indicate whether the determined relative concentrations are within a desired range. The visual indicator may assist an operator by including a display of the relative concentrations or absolute concentration of an oxidant or sterilant as determined and displayed by processing unit 30.

Figure 8:
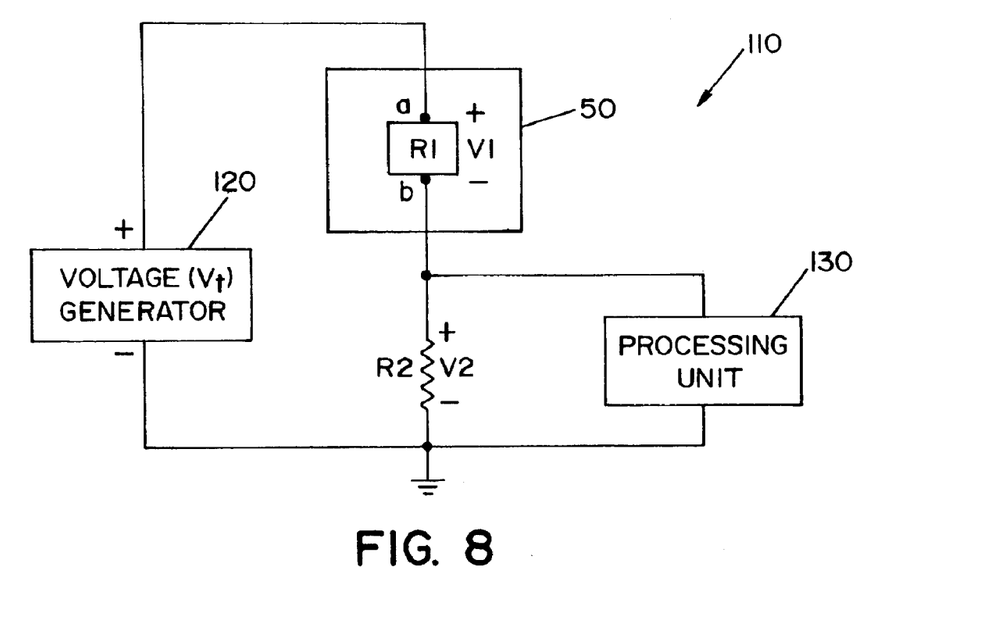
FIG. 8 is a schematic diagram illustrating a chemical concentration measuring system having a resistive voltage divider, according to a alternative embodiment of the present invention.

In an alternative embodiment of the present invention, a measure of electrical resistance is used to determine the relative concentrations of chemical components in a fluid. In this regard, the capacitive voltage divider circuit of the preferred embodiment of the present invention may be suitably replaced with a resistive voltage divider circuit, as shown in FIG. 8.

Chemical concentration measuring system 110 is generally comprised of an input voltage generator 120, a resistor R1, a resistor R2, and a processing unit 130. It should be understood that resistor R1 is representative of the electrical resistance associated with the fluid located between terminals (or electrodes) a and b. Voltage V1 is the voltage across terminals a and b. Resistor R2 is a conventional resistor element. Voltage V2 is the voltage across resistor R2. Resistors R1 and R2 are arranged to form a "resistive" voltage divider circuit, as will be described in further detail below.

Input voltage generator 120 produces an alternating current (AC) input voltage signal, preferably in the form of bi-polar pulses, or radio-frequency (RF) sinusoidal oscillations. The input voltage is applied to resistors R1 and R2. As indicated above, resistor R1 is representative of the electrical resistance associated with the fluid located between terminals a and b. Therefore, resistor R1 acts as a sensing element in a manner similar to capacitor C1 discussed above. Resistor R1 may be located in a conduit, vessel, tank or chamber 50 filled with a liquid or gaseous fluid.

Processing unit 130 measures voltage V2 across resistor R2. In the illustrated embodiment, resistor R2 is outside the fluid. In a preferred embodiment, processing unit 130 may take the form of a microcomputer or microcontroller, including a memory for data storage. Processing unit 130 may also be used to control the operation of other system elements, such as flow controls for controlling the flow of chemical components into conduit, vessel, tank or chamber 50.

Chemical concentration measuring system 110 uses the electrical resistance associated with the fluid to determine the relative concentration of a chemical component in the fluid. Fluid fills the gap between terminals a and b, thereby acting as the resistive element of resistor R1. By arranging resistors R1 and R2 to form a "resistive" voltage divider circuit, a measure of voltage V2 across resistor R2 can be used to determine the resistance associated with resistor R1. In this regard, V1/V2=[R1+R2]/R2, and thus R1=[(V1R2)/V2]−R2. Resistance of resistor R1 is indicative of the relative concentrations of the chemical components in the fluid, since the resistance associated with the fluid is affected by the relative concentrations of the chemical components in the fluid. Resistance values may be collected and stored in tables in the manner discussed above in connection with the capacitive voltage divider. In this regard, resistance values for resistor R1 are determined for fluids having different relative concentrations of chemical components. The data tables can then be used in the same manner as the data tables for the capacitive voltage divider to provide a measure of the concentration of hydrogen peroxide in the fluid.

Figure 9:
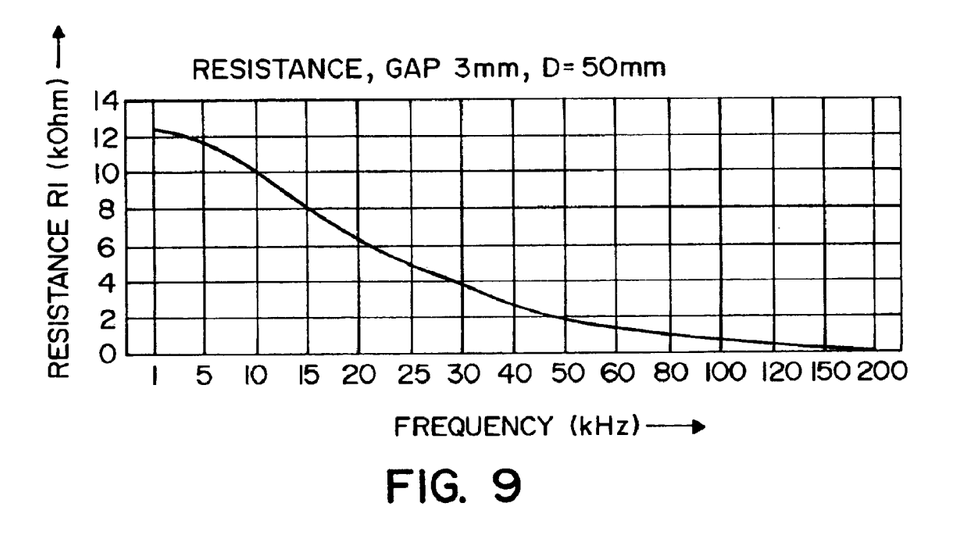
FIG. 9 is a graph illustrating the relationship between resistance of resistor R1 and frequency, for a fluid comprised of water.
Figure 10:
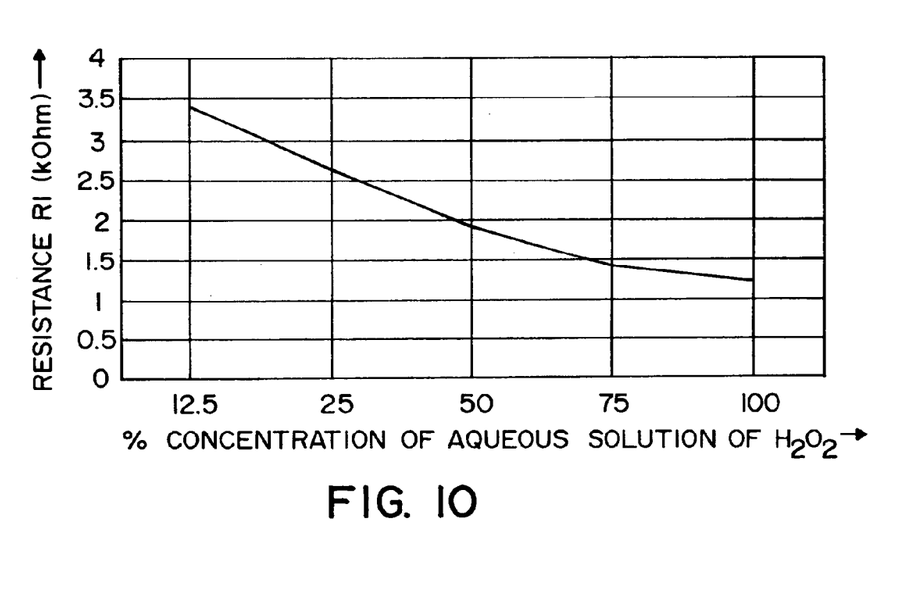
FIG. 10 is a graph illustrating the relationship between: (1) resistance of resistor R1 and relative concentrations of (a) an aqueous solution of hydrogen peroxide and (b) water, at a frequency of 30 kHz.

FIG. 9 is a graph illustrating the relationship between resistance of resistor R1 and frequency, for a fluid comprised of water ($H_2O$). The gap between terminals (or electrodes) a and b is 3 mm, and D=50 mm, where D is the diameter of electrodes a and b. FIG. 10 is a graph illustrating the relationship between: (1) resistance of resistor R1 and (2) relative concentrations of hydrogen peroxide in a fluid comprised of (a) an aqueous solution of hydrogen peroxide and (b) water, at a frequency of 30 kHz. The aqueous solution of hydrogen peroxide is comprised of 35% hydrogen peroxide and 65% water (by weight). The concentrations shown in FIG. 10 are increased from 12.5% aqueous solution of hydrogen peroxide to 100% aqueous solution of hydrogen peroxide.

As indicated above, the present invention finds advantageous application in liquid or vapor sterilization systems. By way of example, an not limitation, a sensing element (i.e., capacitor C1 or resistor R1) of chemical concentration measuring system 10 may be located in a conduit, wherein a feed stream of liquid hydrogen peroxide flows to a vaporization chamber for producing vaporized hydrogen peroxide in a vapor sterilization system. In this manner, the concentration of the liquid hydrogen peroxide in the feed stream for producing the vaporized hydrogen peroxide can be verified. A sensing element (i.e., capacitor C1 or resistor R1) of chemical concentration measuring system 10 could alternatively be located in a treatment chamber containing vaporized hydrogen peroxide or liquid hydrogen peroxide. In this manner, the concentration of the hydrogen peroxide can be monitored during a sterilization process. Furthermore, a control system may be programmed to respond to the measured concentration of hydrogen peroxide with modifications to system operating parameters, to increase or decrease the hydrogen peroxide concentration in the treatment chamber, or to alert an operator to unsuitable sterilization conditions.

Other modifications and alterations will occur to others upon their reading and understanding of the specification. In this regard, while the present invention has been described with reference to liquid and vapor sterilization systems, it is contemplated that the present invention may be advantageously employed in other applications, including, but not limited to, etching systems for semiconductor manufacture. Furthermore, it should be appreciated that the capacitive and resistive voltage divider circuits described herein may be substituted with other circuits that measure capacitance and Having described the invention, the following is claimed:

1. A chemical concentration measuring system used in a biocontamination deactivation apparatus having a vaporizer that receives a feed stream comprised of a fluid having hydrogen peroxide and at least one chemical component, wherein the chemical concentration measuring system determines the concentration of the hydrogen peroxide in the fluid, the system comprising:

sensing means responsive to changes in the concentration of the hydrogen peroxide in the fluid, the sensing means including a capacitive voltage divider circuit including:
   (a) a first capacitor having first and second conductors exposed to the fluid, said fluid comprising a dielectric therebetween, and
   (b) a second capacitor;

an alternating current (AC) voltage generator for applying an AC voltage to the capacitive voltage divider circuit;

a memory for storing a table of data including capacitance values and corresponding concentration values indicative of the relative concentration of hydrogen peroxide in the fluid; and processing means for measuring a voltage across the second capacitor to determine a capacitance value associated with the first capacitor, and determining the concentration of the hydrogen peroxide in the fluid using the determined capacitance value and the table of data stored in the memory.

2. A chemical concentration measuring system according to claim 1, wherein said first capacitor is selected from the group consisting of: a parallel plate capacitor, a cylindrical capacitor, and a spherical capacitor.

3. A chemical concentration measuring system according to claim 2, wherein said first capacitor is a parallel plate capacitor, said first and second conductors being metal net plates.

4. A chemical concentration measuring system according to claim 1, wherein said processing means obtains a relative concentration of the hydrogen peroxide using said table of data.

5. A chemical concentration measuring system according to claim 4, wherein said processing means normalizes said relative concentration of the hydrogen peroxide to provide an absolute concentration of the hydrogen peroxide in the fluid.

6. A chemical concentration measuring system according to claim 1, wherein said processing means interpolates or extrapolates a relative concentration of the hydrogen peroxide using said table of data.

7. A chemical concentration measuring system according to claim 1, wherein said at least one chemical component is liquid water.

8. A chemical concentration measuring system used in a biocontamination deactivation apparatus having a vaporizer that receives a feed stream comprised of a fluid having hydrogen peroxide and at least one chemical component, wherein the chemical concentration measuring system determines the concentration of the hydrogen peroxide in the fluid, the system comprising:

sensing means responsive to changes in the concentration of the hydrogen peroxide in the fluid, the sensing means including a resistive voltage divider circuit including:
   (a) a first resistor including first and second conductors exposed to the fluid, said fluid comprising a resistive element of the first resistor, and
   (b) a second resistor;

a memory for storing a table of data including resistance values and corresponding concentration values indicative of the relative concentration of hydrogen peroxide in the fluid;

an alternating current (AC) voltage generator for applying an AC voltage to the resistive voltage divider circuit; and processing means for measuring a voltage across the second resistor to determine a resistance value associated with the first resistor, and determining the concentration of the hydrogen peroxide in the fluid using the determined resistance value and the table of data stored in the memory.

9. A chemical concentration measuring system according to claim 8, wherein said processing means obtains a relative concentration of the hydrogen peroxide using said table of data.

10. A chemical concentration measuring system according to claim 9, wherein said processing means normalizes said relative concentration of the hydrogen peroxide to provide an absolute concentration of the hydrogen peroxide in the fluid.

11. A chemical concentration measuring system according to claim 8, wherein said processing means interpolates or extrapolates a relative concentration of the hydrogen peroxide using said table of data.

12. A chemical concentration measuring system according to claim 8, wherein said at least one chemical component is liquid water.

13. A method for determining a concentration of hydrogen peroxide in a feed stream received by a vaporizer for a biocontamination deactivation apparatus, wherein the feed stream is comprised of a fluid having hydrogen peroxide and at least one chemical component, the method comprising:

exposing a capacitor, of a capacitive voltage divider circuit, to the fluid, wherein said fluid comprises a dielectric between first and second conductors of the capacitor, said capacitor having an associated voltage that varies according to the concentration of the hydrogen peroxide in the fluid;

pre-storing data in a memory, including capacitance values associated with the capacitor and corresponding concentration values that are indicative of the concentration of the hydrogen peroxide in the fluid;

measuring the associated voltage;

determining a capacitance value associated with the capacitor using the measured associated voltage; and accessing said pre-stored data using the capacitance value to determine the relative concentration of the hydrogen peroxide in the fluid.

14. A method according to claim 13, wherein said method further comprises:

interpolating or extrapolating from the table of data a relative concentration of the hydrogen peroxide in the fluid, corresponding to the capacitance value associated with the capacitor.

15. A method according to claim 13, wherein said method further comprises:

normalizing said relative concentration to provide an absolute concentration of the hydrogen peroxide in the fluid.

16. A method according to claim 13, wherein said at least one chemical component is liquid water.

17. A method for determining a concentration of hydrogen peroxide in a feed stream received by a vaporizer for a biocontamination deactivation apparatus, wherein the feed stream is comprised of a fluid having hydrogen peroxide and at least one chemical component, the method comprising:

exposing a resistor, of a resistive voltage divider circuit, to the fluid, wherein said fluid comprises a resistive element of the resistor between first and second conductors of the resistor, said resistor having an associated voltage that varies according to the concentration of the hydrogen peroxide in the fluid;

pre-storing data in a memory, including resistance values associated with the resistor and corresponding concentration values that are indicative of the concentration of the hydrogen peroxide in the fluid;

measuring the associated voltage;

determining a resistance value associated with the resistor using the measured associated voltage; and accessing said pre-stored data using the resistance value to determine the relative concentration of the hydrogen peroxide in the fluid.

18. A method according to claim 17, wherein said method further comprises:

interpolating or extrapolating from the table of data a relative concentration of the hydrogen peroxide in the fluid, corresponding to the resistance value associated with the resistor.

19. A method according to claim 17, wherein said method further comprises:

normalizing said relative concentration to provide an absolute concentration of the hydrogen peroxide in the fluid.

20. A method according to claim 17, wherein said at least one chemical component is liquid water.

* * * * *